(12) United States Patent
Hall

(10) Patent No.: US 8,015,648 B2
(45) Date of Patent: Sep. 13, 2011

(54) SYSTEM FOR REMOVABLY JOINING A DRIVEN MEMBER TO A DRIVEN MEMBER WITH WORKPIECE

(75) Inventor: Scott E. Hall, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1164 days.

(21) Appl. No.: 10/539,700

(22) PCT Filed: Dec. 3, 2003

(86) PCT No.: PCT/IB03/05681
§ 371 (c)(1),
(2), (4) Date: Jun. 16, 2005

(87) PCT Pub. No.: WO2004/054467
PCT Pub. Date: Jul. 1, 2004

(65) Prior Publication Data
US 2006/0150349 A1    Jul. 13, 2006

Related U.S. Application Data

(60) Provisional application No. 60/434,609, filed on Dec. 18, 2002.

(51) Int. Cl.
*A46B 13/02* (2006.01)
*A61C 17/22* (2006.01)
(52) U.S. Cl. .................................................... 15/22.1
(58) Field of Classification Search ................... 15/22.1; 310/50
See application file for complete search history.

(56) References Cited

U.S. PATENT DOCUMENTS

| 4,103,511 | A | | 8/1978 | Kress et al. |
| 4,777,393 | A | | 10/1988 | Peot |
| 5,617,601 | A | * | 4/1997 | McDougall ..................... 15/22.1 |
| 5,848,841 | A | | 12/1998 | Wu |
| 6,248,059 | B1 | * | 6/2001 | Gamper et al. ................. 600/38 |
| 2002/0162180 | A1 | * | 11/2002 | Blaustein et al. ............... 15/22.1 |
| 2005/0050658 | A1 | * | 3/2005 | Chan et al. ..................... 15/22.1 |

FOREIGN PATENT DOCUMENTS

| FR | 2169457 | * | 9/1973 |
| JP | 5018467 | | 6/1948 |
| JP | 02084526 A | | 3/1990 |
| JP | 05137615 A | | 6/1993 |
| JP | 10-235574 | * | 10/1998 |

* cited by examiner

*Primary Examiner* — Randall Chin
(74) *Attorney, Agent, or Firm* — Daniel Sheridan

(57) ABSTRACT

The system includes a plurality of joining assemblies (37, 38, 39) for removably attaching a driven member assembly (15) of the appliance to an appliance body portion (12), wherein the joining assemblies are separate from the torsional axis of the workpiece. The joining assemblies each include an extending pin member (43) on the appliance body and a receiving element (46) in the driven member assembly for receiving the extending pin member. A drive shaft (16) for the workpiece is connected to a head portion (24) of the driven member assembly by two springs (32, 34), wherein the extending pin member mates with the receiving element in such a manner that there is no lost motion of the workpiece during operation but also such that the driven member assembly is readily removable from the appliance body.

16 Claims, 3 Drawing Sheets

SYSTEM FOR REMOVABLY JOINING A DRIVEN MEMBER TO A DRIVEN MEMBER WITH WORKPIECE

CROSS REFERENCE TO RELATED APPLICATION

This application claims the benefit of U.S. provisional application Ser. No. 60/434,609 filed Dec. 18, 2002, which is incorporated herein by reference.

This invention relates generally to small appliance devices, including personal care appliances, and more specifically concerns a structure for joining a driven member assembly portion of such an appliance, which includes a workpiece, and the remainder of the appliance, such as an appliance base/body portion, which contains a driving member for the appliance.

Personal care appliances, for example, a power toothbrush or shaver, or other small power appliances such as a blender or mixer, will typically have a base portion, which includes a driving member for the appliance, such as a motor, and a driven member assembly, which includes a workpiece element of some kind. A power toothbrush will include a handle portion with a driving member and a removable head portion with a driven member assembly which includes a brushhead with bristles thereon. An attachment or coupling structure is necessary to interface these two portions of the appliance.

The arrangement/configuration of the coupling structure depends upon the particular motion transmitted to the driven member by the driving member. In those systems in which the workpiece is driven by torsion action, i.e. a unidirectional or a back-and-forth twisting action, the driven member assembly may, in one embodiment for example, include a spring or other return element which connects a drive shaft on which the workpiece is mounted to an appliance head portion, or in another embodiment include a spring member which clamps the workpiece with the head portion onto the drive shaft.

In such systems, the spring force of the clamping member relative to the drive shaft should be high enough that the clamping member will not temporarily separate from the drive shaft during a portion of the drive shaft movement, which results undesirably in loss of efficiency (lost motion) and substantial noise. The clamping force to achieve such a result, however, has the undesirable result of making removal and insertion of the workpiece relative to the drive shaft, such as in changing brushheads, very difficult, i.e. the force required is too high for convenient removal by most users.

It would thus be desirable to have a coupling structure which does not produce lost motion between the driving member, usually a drive shaft of some kind, and the driven member, and which is substantially noiseless, while at the same time the driven member assembly can be readily removed from the base portion of the appliance carrying the driving member.

Accordingly, the present invention is a system for joining an appliance body having a driving assembly therein to a driven member assembly which includes a workpiece element having a torsional axis of movement, comprising: a plurality of joining assemblies for removably attaching said driven member assembly to said appliance body, wherein the joining assemblies are each separate from the torsional axis of the workpiece element, wherein the joining assemblies each include a mating member on one of a) the appliance body or b) the driven member assembly and an associated receiving element on the other thereof, wherein the mating members and the receiving elements have such a configuration, respectively, and mate in such a manner that there is substantially no lost motion for the workpiece element during operation of the appliance and such that the driven member assembly is readily removable from the appliance body.

FIG. 1 shows the appliance coupling system of the present invention, in a power toothbrush application for illustration. It should be understood that the present invention could be used with other personal care appliances such as a shaver, or in other small appliances, such as power tools and/or kitchen appliances, including blenders or mixers.

Figure 1:
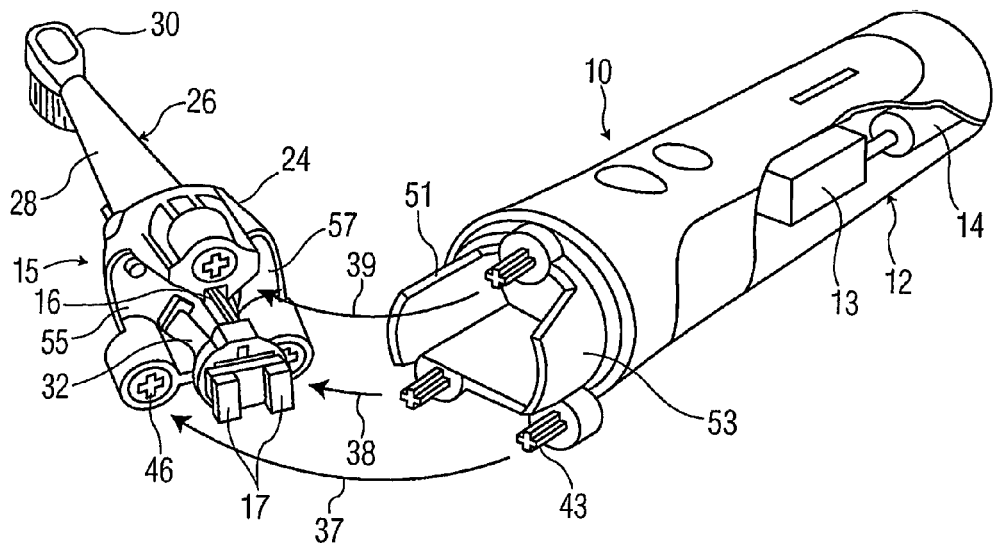
FIG. 1 is an exploded perspective view showing the coupling system of the present invention in a power toothbrush application.

The power toothbrush 10 of FIG. 1 includes an elongated base/handle portion 12, which includes an electromagnetic driving member 13 therein, along with a battery 14, although other driving arrangements can be used, including motors. In the particular embodiment shown, electromagnetic driver 13 drives the rear end of a drive shaft 16, which is part of a driven member assembly 15, and on which is mounted a pair of permanent magnets 17-17 in a side-to-side, back-and-forth motion. This driving action is described in detail in U.S. Pat. No. 5,189,751, the contents of which are hereby incorporated by reference.

Drive shaft 16 extends upwardly through the driven member assembly which includes what is referred to as a head portion 24. A workpiece 26 is mounted on the extending end of drive shaft 16. In the embodiment shown, workpiece 26 includes a mounting arm 28 and a brushhead 30. A base part 19 of drive shaft 16 is connected by two flat spring members 32 and 34 to head portion 24. This arrangement results in the conversion of the side-to-side motion of the rear end of drive shaft 16 provided by electromagnetic driver 13 to an arcuate motion over a defined angle, e.g. 8-14.degree. Such a structure is described in detail in U.S. Pat. No. 7,067,945, owned by the assignee of the present invention, the contents of which are incorporated by reference. The arcuate action of drive shaft 16 results in a torque on the head portion 24 through the two spring members 32 and 34.

The coupling system of the present invention is designed to prevent lost motion of drive shaft 16 as it rotates back and forth through the specified arc. The coupling system includes three spaced joining assemblies 37-39 (shown by arrows) between the base portion 12 and head portion 24. The three joining assemblies 37-39 in the embodiment shown are all located around the periphery of the interface between the head portion and the base portion and are separate from the axis of the drive shaft 16. Two joining assemblies 37, 38 are separated by approximately ⅞ inch, while the third joining assembly 39 forms a triangular relationship with assemblies 37, 38, separated by approximately 1⅛ inches from each of those two joining assemblies, respectively. This arrangement, however, can be varied.

Each joining assembly comprises an elongated pin member 43, which is positioned at and extends from the upper surface of the base portion of the appliance. In the embodiment shown, pin member 43 is approximately 5/16 inch long and is approximately 3/16 inch thick, at its thickest point. In the embodiment shown, pin member 43 has a cross-like cross-section, although this again can be varied. Pin member 43 fits into a mating receptacle 46 positioned in the lower part of the head portion 24 of the appliance. Receptacle 46 can be a separate part, installed in an opening in the head portion, or can be formed directly in the head portion. The pin 43 fits firmly into the receptacle 46, which has a cross-sectional configuration which mates with the cross-sectional configuration of pin 43.

The receptacle and the pin are configured so that there is an interference fit between the receptacle and the pin such that receptacle 46 is deformed during insertion of pin 43 to the extent that a predicted compression force is placed on pin 43. This force is across two opposing portions (blades) of pin 43 when the pin is in the shape of a cross. The compression force is across an individual (single) blade if element 43 is a single blade, and is directed toward the center of the element 43 if the element is circular.

With all the above configurations, the result is a balanced set of compression forces on the joining assemblies that maintain the driven member assembly in place. When a load is applied by operation of the driving assembly, the balance of the forces shifts as the joining assemblies react to the load. None of the compression forces go to zero because the increase of the reaction forces due to the load action. Accordingly, the mating surfaces remain clamped together. Otherwise, the two surfaces would separate for a brief time and the alternating torque would result in a rapid opening and closing of the two surfaces, producing an unpleasant noise during operation of the appliance.

It is thus important that the two members be designed for a relatively tight fit, so that the action between the two members will be as explained above and that the torsional force on the head portion produced by action of the drive shaft and the two spring members connected to the head portion will not result in any motion between the head portion and the base portion of the appliance and hence there will be no lost motion of the drive shaft.

As explained above, the joining assemblies are not coincident with the torsional axis of the appliance, i.e., the axis of drive shaft 16. In the present arrangement, the physical distance between the three static joining assemblies and the torsional axis of the workpiece results is a significant mechanical advantage for the joining assemblies. The forces required to resist the torque produced by the driving action are such with the arrangement shown that a no lost motion result is achieved without the need for such an extremely tight fit that a large force is necessary to install or remove the head portion. The head portion is conveniently removable by a typical user, yet there is no lost motion during action of the appliance because of the particular pin/receptacle joining structure described above. The noise produced by the arcuate action of the appliance is also minimal.

The distance between the respective joining assemblies 37-39 results in a broad support base, which improves the stability of the coupling structure. Since the coupling structure is in effect static, another part, which may be an adapter or other accessory, such as a fitting to join a larger or smaller head portion to an existing handle can be used between the appliance base portion and the driven member assembly. The accessory moves with the drive shaft 16. The type and movement of the accessory is limited by the power available from the driving member.

In use, drive shaft 16 is moved through its action by the driving assembly, either by direct action, such as a motor, or other means, such as magnetic action, without resulting in relative movement between the head portion, to which the drive shaft is secured by means of the spring elements, and the base portion of the appliance. Since there is no lost motion, the device is quiet in operation.

While the embodiment shown includes three spaced joining assemblies, two spaced joining assemblies, either opposed or spaced in some other arrangement, can be successfully used. More than three joining assemblies can also be used. However, three such assemblies is preferred, for reliable action with economy of structure.

Figure 5:
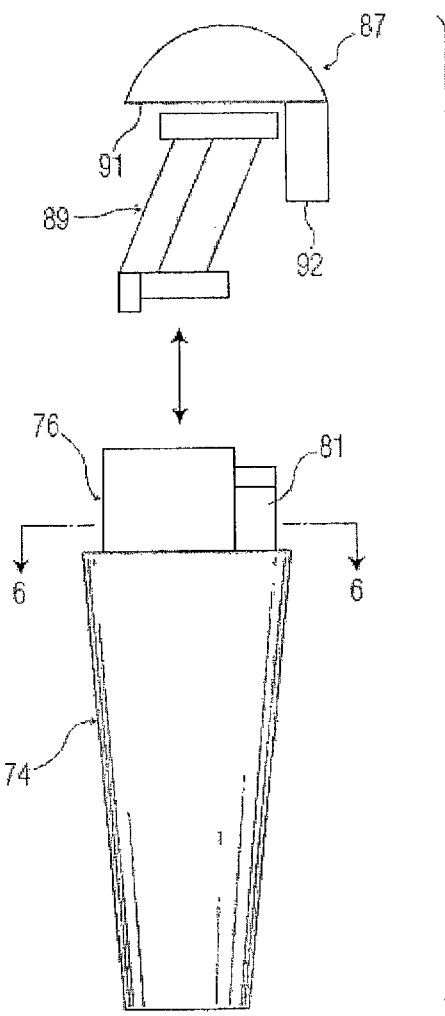
FIG. 5 is an exploded view of a portion of an appliance showing another embodiment of the present invention.
Figure 6:
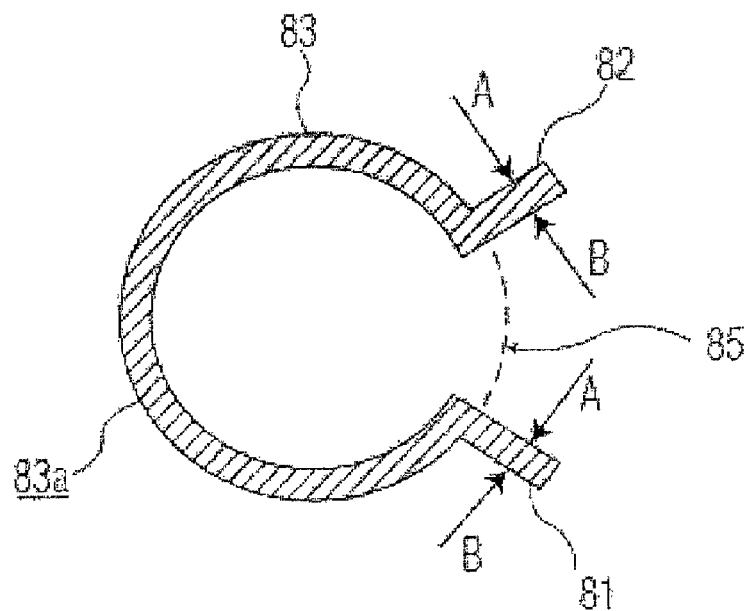
FIG. 6 is a cross-section view along lines 6-6 of FIG. 5.
Figure 7:
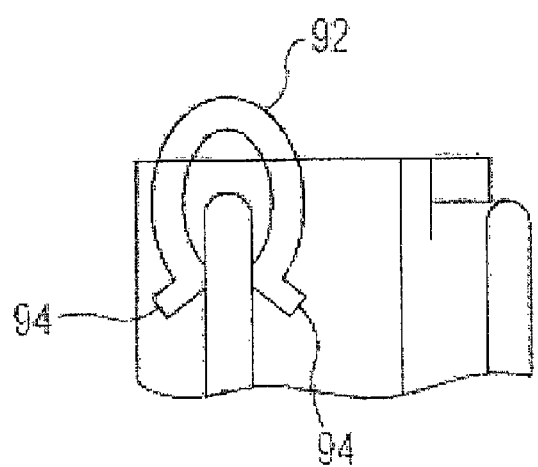
FIG. 7 is an elevational view showing the spring clamping action of the embodiment of FIGS. 5 and 6.

In general, the coupling structure of the present invention comprises a plurality of joining assemblies which attach a head portion of an appliance to a base portion of the appliance, the base portion including a driving assembly. The joining assemblies are spaced apart from the torsional axis of the device, specifically the drive shaft on which is mounted the workpiece. There is no lost motion with such an arrangement and yet decoupling of the two portions is relatively easy and does not require high force/effort. FIG. 1 shows one example of such a system. FIGS. 5-7 show another embodiment, which is described below.

The coupling structure also includes a registration arrangement to ensure that the two portions are coupled together in proper orientation. A non-symmetric arrangement of the joining assemblies would also accomplish an orientation function. The registration structure shown includes two opposed ear members 51, 53, both relatively thin, which extend upwardly from the periphery of the base portion. The ear members fit into mating spaces 55, 57. The ears and spaces are configured such that the two portions can fit together in only one arrangement and result in a more "automatic" or easy coupling of the two appliance portions.

Figure 4:
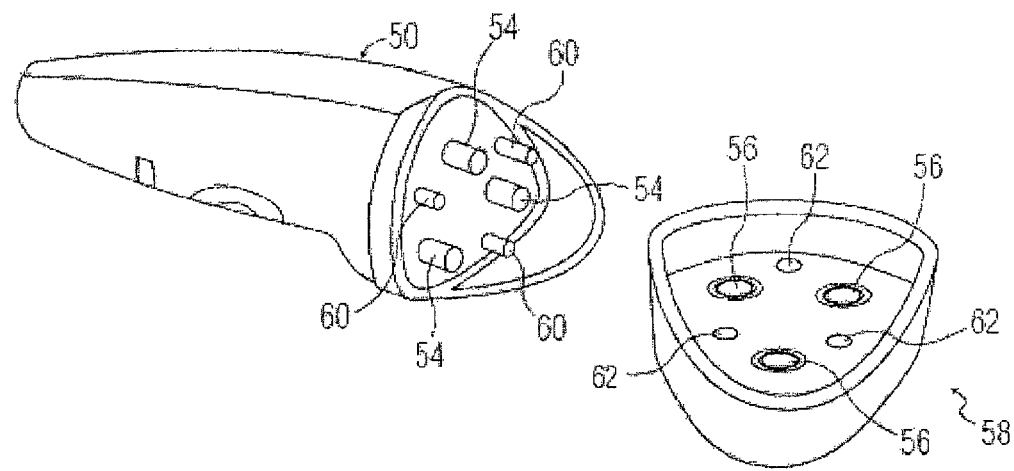
FIG. 4 is a perspective view showing the system of the present invention in a shaver application.

FIG. 4 shows the coupling structure of the present invention in a power shaver application, illustrating its usefulness in other appliances besides a power toothbrush. The shaver includes a body portion 50, which contains a driving assembly, such as a motor, therein. The motor drives three drive shafts 54-54, which fit into blade assemblies 56-56, positioned in a shaver head portion 58. Extending from an upper surface of appliance body 50 are three spaced friction pins 60-60 mounted around the periphery of the appliance body. Friction pins 60-60 extend into and mate with corresponding receiving openings 62-62 in the shaver head portion. Friction pins 60 engage the receiving openings 62, and the three drive shafts engage the individual blade assemblies 56. The combination of the three pins and their associated receiving openings prevent lost motion of the drive shaft and therefore minimize noise of the apparatus during operation.

FIGS. 5, 6 and 7 show another embodiment of the present invention. The elements shown on those figures are for a power toothbrush, but other appliances can be used. In this embodiment, a cup-like portion 76 at the upper end of a handle portion 74 of a power appliance includes two separate rib portions 81 and 82 which extend radially outward from circular wall 83 of the cup portion 76. FIG. 6 shows cup wall 83 having a part 85 between ribs 81 and 82 removed (so there is an open space between the ribs), but alternatively, the cup wall 83 could be continuous, with ribs 81 and 82 extending radially outward from an outer surface 83a of wall 83.

A head portion 87 of the appliance fits down over the cup portion 76, mating with the handle portion 74. Drive spring assembly 89 is positioned within the cup portion of the handle as the head and handle mate together, with the drive spring 89 being driven by electromagnetic action from a drive unit within handle 74.

Extending downwardly from lower edge 91 of head portion are two spring receptacles 92, shown most clearly in FIG. 7. The spring receptacles 92 (one for each rib) are generally hoop-like in configuration with an open section at an end thereof and small protuberances 94-94 extending from the respective ends of the receptacle. The free ends of the hoop tend to spring toward each other. The receptacles 92 are positioned on head 87 to extend over ribs 81, 82 and to provide a spring force against the ribs. In the embodiment shown, there are two ribs and two mating spring receptacles. However, it should be understood that additional ribs/receptacle combinations can be used.

Figure 2:
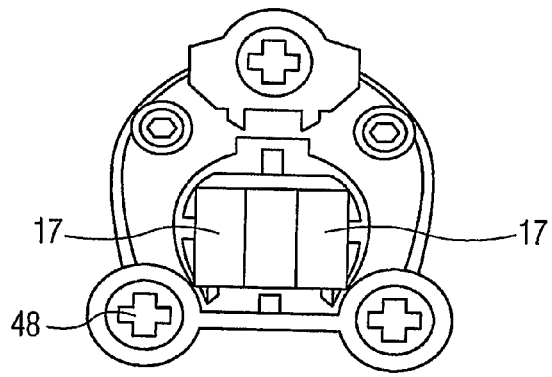
FIG. 2 is an end view of the driven member assembly portion of the appliance of FIG. 1 showing the arrangement between the drive shaft on which the workpiece is mounted and the removable head portion.
Figure 3:
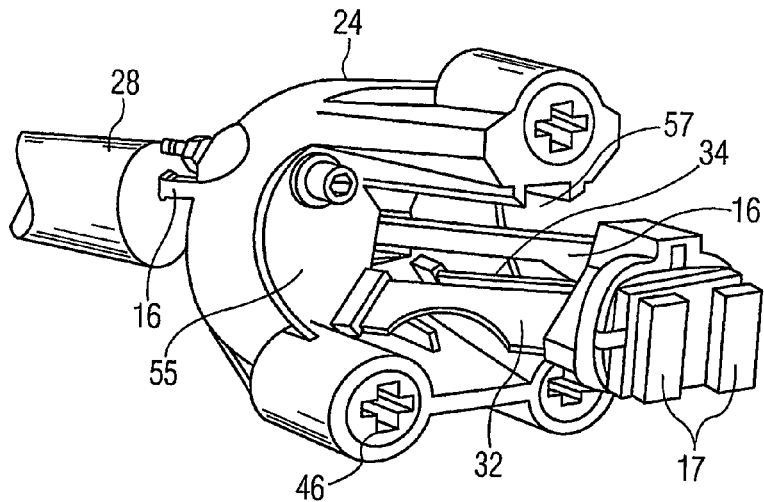
FIG. 3 is a perspective view of the driven motor assembly.

In operation, the spring force exerted by the receptacles on the ribs in the "A" direction in FIG. 6 increase during clockwise torque produced by movement of the workpiece drive spring assembly; hence, the spring force on the ribs in the "B" direction will decrease, which tends to prevent separation of the spring receptacles from the ribs during operation of the device, resulting in quiet operation of the appliance. The spring/rib arrangement provides the desired high resistance against such separation (no lost motion), while at the same time permitting convenient insertion/removal of the head from the handle, as with the embodiment of FIGS. 1-3.

Although a preferred embodiment of the invention has been described for purposes of illustration, it should be understood that various changes, modification and substitutions might be incorporated in the embodiment without departing from the spirit of the invention, which is defined in the claims, which follow.

The invention claimed is:

1. A system for joining an appliance body of an appliance to a driven member assembly, the appliance body having a driving assembly therein, the driven member assembly including a workpiece element having a torsional axis of movement, comprising:
   a plurality of joining assemblies removably attaching the driven member assembly to the appliance body, wherein the joining assemblies are each separate from the torsional axis of the workpiece element,
   wherein the joining assemblies each include a mating member on one of a) the appliance body and b) the driven member assembly and an associated receiving element on the other thereof, wherein the mating members and the receiving elements have such a configuration, respectively, and mate in such a manner that there is substantially no lost motion for the workpiece element during operation of the appliance and such that the driven member assembly is readily removable from the appliance body upon application of an axial force,
   wherein the mating members comprise protrusions having a substantially cross-shaped cross-section, the receiving elements comprise receptacles having a substantially cross-shaped cross-section, and the mating members are adapted to slidably engage with the receiving elements, and
   wherein the mating of the mating members and the receiving elements is an interference fit.

2. A system of claim 1, wherein the configuration of the mating members and receiving elements is such that compression forces sufficient to maintain contact therebetween are always present during torque action of a drive shaft on which the workpiece is mounted.

3. A system of claim 1, including three spaced joining assemblies located around the periphery of the interface between the appliance body and the driven member assembly.

4. A system of claim 1, wherein the mating member of each joining assembly has a non-circular cross-section and the associated receiving element has a similar non-circular cross-section, such that the receiving element and the mating member are capable of mating together.

5. A system of claim 1, wherein the appliance body and the driven member assembly, respectively, include a handle portion and a head portion of an oral care appliance.

6. A system of claim 5, wherein the oral care appliance is a power toothbrush.

7. A system of claim 1, including registration elements on the appliance body which mate with the driven member assembly, the registration elements producing a proper orientation between the appliance body and the driven member assembly as the appliance body is joined to the driven member assembly.

8. A system of claim 1, wherein the mating member extends from the appliance body and the receiving element is in the driven member assembly.

9. A system of claim 1, wherein the mating members comprise spaced blade elements in the appliance body and the receiving elements comprise spring assemblies which clamp onto the blade elements with a compression force.

10. An oral care appliance, comprising:
    an appliance body having a driving assembly therein;
    a driven member assembly which includes a workpiece element having a torsional axis of movement and wherein the workpiece element includes a brushhead; and
    a coupling structure for joining the appliance body to the driven member assembly, the coupling structure including a plurality of joining assemblies removably attaching the driven member assembly to the appliance body, wherein the joining assemblies are each separate from the torsional axis of the workpiece element,
    wherein each joining assembly includes a mating member on one of a) the appliance body and b) the driven member assembly and an associated receiving element in the other thereof, receiving said mating member, wherein the mating members and the receiving elements have such a configuration, respectively, and mate in such a manner that there is substantially no lost motion for the workpiece element during operation of the appliance, and such that the driven member assembly is readily removable from the appliance body upon application of an axial force,
    wherein the mating members comprise protrusions having a substantially cross-shaped cross-section, the receiving elements comprise receptacles having a substantially cross-shaped cross-section, and the mating members are adapted to slidably engage with the receiving elements, and
    wherein the mating of the mating members and the receiving elements is an interference fit.

11. An appliance of claim 10, including three spaced joining assemblies arranged around the periphery of the interface between the appliance body and the driven member assembly.

12. An appliance of claim 10, wherein the mating member of each joining assembly has a non-circular cross-section and the associated receiving element has a similar non-circular cross-section, such that the receiving element and the mating member are capable of mating together.

13. An appliance of claim 10, wherein the mating member extends from the appliance body and the receiving element is in the driven member assembly.

14. An appliance of claim 10, wherein the mating members include spaced blade elements in the appliance body and the receiving elements comprise spring assemblies which clamp onto the blade elements with a compressive force.

15. A brushhead-handle assembly of a power toothbrush in which a brushead is joinable to and removable from a handle portion of the toothbrush by a plurality of joining assemblies, the joining assemblies being separate from a torsional axis of movement of a brushhead workpiece portion of the brushhead assembly, comprising:

a brushhead assembly which includes a brushhead workpiece element, wherein the brushhead assembly includes a plurality of first joining members which mate with associated second joining members in the handle portion to form joining assemblies, wherein the first joining members have such a configuration, relative to the configuration of the associated second joining members and mate therewith in such a manner that there is substantially no lost motion of the workpiece element during operation of the toothbrush and such that the brushhead assembly is readily removable from the handle portion of the toothbrush upon application of an axial force, wherein the associated second joining members comprise protrusions having a substantially cross-shaped cross-section, the first joining members comprise receptacles having a substantially cross-shaped cross-section, and the associated second joining members are adapted to slidably engage with the first joining members, and wherein the mating of the joining members and the first second joining members is an interference fit.

16. The brushhead-handle assembly of claim 15, wherein the configuration of the first joining elements and the second joining members are such that compression forces sufficient to maintain contact therebetween are always present during torque action of a drive shaft on which the workpiece portion is mounted.

* * * * *